United States Patent [19]

Kottenhahn et al.

[11] Patent Number: 5,608,076

[45] Date of Patent: Mar. 4, 1997

[54] METHOD OF PREPARING AMIONOAKYLHYDANTOINS AND AMINOALKYL-ALPHA-AMINO ACIDS

[75] Inventors: Matthias Kottenhahn; Karlheinz Drauz, both of Freigericht; Andreas Bommarius, Frankfurt, all of Germany

[73] Assignee: Degussa Aktiengesellschaft, Frankfurt, Germany

[21] Appl. No.: 416,855

[22] PCT Filed: Oct. 8, 1993

[86] PCT No.: PCT/EP93/02753

§ 371 Date: May 23, 1995

§ 102(e) Date: May 23, 1995

[87] PCT Pub. No.: WO94/08974

PCT Pub. Date: Apr. 28, 1994

[30] Foreign Application Priority Data

Oct. 16, 1992 [DE] Germany .............................. 4234867.6

[51] Int. Cl.$^6$ ...................... C07D 233/76; C07D 233/72; A61K 31/415
[52] U.S. Cl. ...................... 548/317.1; 548/320.1
[58] Field of Search ............................ 548/320.1

[56] References Cited

U.S. PATENT DOCUMENTS

| | | | |
|---|---|---|---|
| 2,564,649 | 8/1954 | Rogers | 548/320.1 X |
| 2,870,201 | 1/1959 | Pollack | 548/320.1 X |
| 3,078,274 | 2/1963 | Rogers | 548/320.1 |
| 3,452,040 | 6/1969 | Langis | 540/320.1 |
| 3,456,000 | 7/1969 | Langis | 548/320.1 X |

FOREIGN PATENT DOCUMENTS

| | | | |
|---|---|---|---|
| 2855937 | 7/1980 | Germany | 548/320.1 |
| 4234867 | 4/1994 | Germany | 548/320.1 |

OTHER PUBLICATIONS

Drauz, et al: "Chemoenzymatische Synthese von N–Carbamoyl–D–4–thialysin and N–Carbamoyl–D–homo–5–thialysin" (1992).

Drauz, et al: "Chemoenzymatische syntheses of omega–ureido D–amino acids" (1991).

Sobczyk, et al: "13C NMR spectra of hydantoins and 3–phanyl–2–thiohydantoins of amino acids", Polish Journal of Chemistry, vol. 54, No. 9, 1980.

*Primary Examiner*—Floyd D. Higel
*Attorney, Agent, or Firm*—Cushman Darby & Cushman IP Group of Pillsbury Madison & Sutro LLP

[57] ABSTRACT

The invention relates to a method of preparing 5-(aminoalkyl)-hydantoins with basic side chain in which the protection of the amino function in the side chain is necessary during the formation of the hydantoin requires minimal expense.

5 Claims, 1 Drawing Sheet

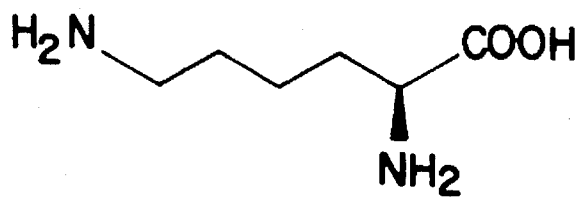
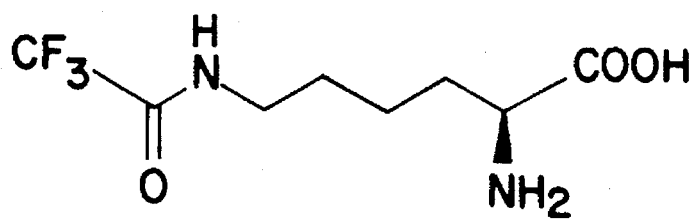
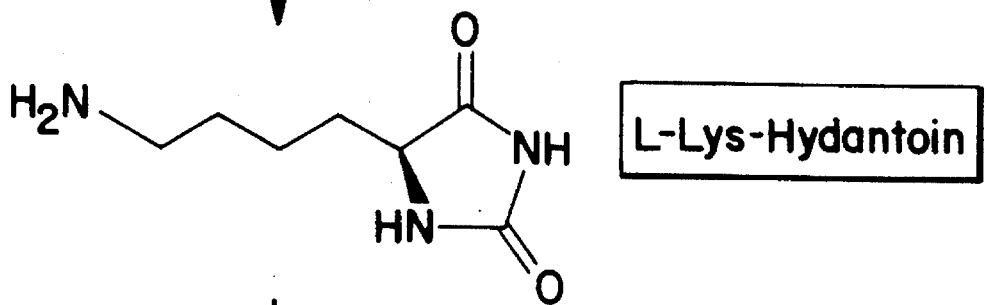
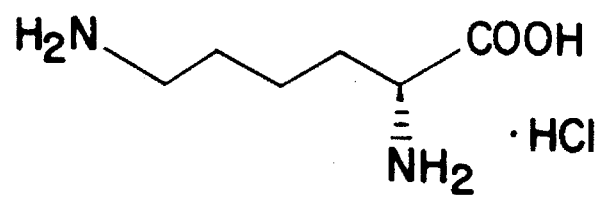

METHOD OF PREPARING AMIONOAKYLHYDANTOINS AND AMINOALKYL-ALPHA-AMINO ACIDS

The present invention relates to a method of preparing 5-(aminoalkyl)-hydantoins of the general formula I or the aminoalkyl-α-amino acids of the general formula II or their salts obtainable from them

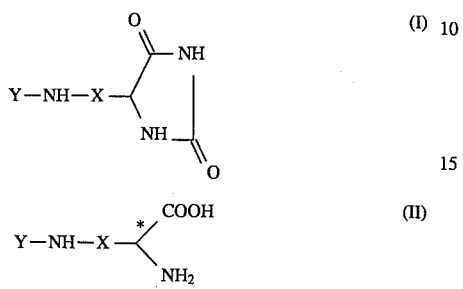

in which
- X stands for a $C_1$–$C_6$ alkylene group which can be substituted and/or interrupted by heteroatoms such as, for instance, sulfur or oxygen (i.e., the alkylene group may be substituted by heteroatoms as demonstrated in Formula I or the heteroatom may fit in the alkylene group as shown in Formula II), with preservation of the adjacent amino function and Y stands for hydrogen or an organic group with up to 8 C atoms which can be substituted and/or interrupted by heteroatoms, such as, for instance, sulfur or oxygen, with preservation of the X and Y adjacent amino function and
- \* signifies an optically pure compound on the α-C atom.

In describing X as a $C_1$–$C_6$ alkylene group which can be substituted and/or interrupted by heteroatoms it is meant that the alkylene group may be substituted by heteroatoms as shown immediately below in FIG. 1 or the heteroatom may fit in the alkylene group as shown immediately below in FIG. 2.

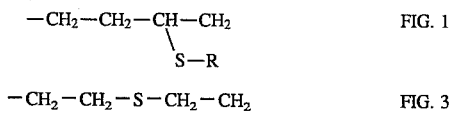

The synthesis of amino acids via the corresponding hydantoins is a known method of procedure. Thus, for example, α-amino acids can be cyclized with cyanate or cyanohydrins with ammonium hydrogen carbonate to the corresponding hydantoin (5-substituted imidazolidine-2,4-dione). The hydantoins can basically be split by means of chemical hydrolysis into the D,L amino acids, by means of enzymatic hydrolysis selectively into the D- or L-amino acids. Corresponding methods are known, for example, from DE 39 17 057 C and EP 0,377,083 A. In particular, the stereospecific splitting of the hydantoins is especially interesting since the D-antipodes of natural amino acids can be prepared as a result thereof. As is known from Ch. Syldatk et al. Adv. Biochem. Eng. 44, 29–75, 40 (1990), the corresponding preparation of amino acids with charged side chains poses problems. Thus, A. Moller et al., Enzyme Microb. Techol. 10, also found a broad hydantoinase and carbamoylase activity in the bacterium Arthrobacter crystallopaites AM2; however, hydantoins with charged side chains, including among others the hydantoins of lysine and ornithine, were not converted. On the other hand, the conversion of basic hydantoins is sporadically suggested (DE 39 17 057 C) and described (S. Takahashi et al., J. Ferment. Technol. 56, 492–8 (1978) and 57, 328 (1979); however, in the latter instance the conversion takes place only up to the carbamoyl-D-lysine. It basically turned out that, if at all, only the derivatives unprotected on the amino function are received as substrates during the enzymatic conversion. Thus, for example, corresponding amides such as 5-(4'-(N-carbobenzoxyamino)-butyl)-hydantoin are not converted with Agrobacterium radiobacter whereas the correspondingly unprotected 5-(4'-aminobutyl)-hydantoin is recognized as substrate. This has the consequence that correspondingly protected aminoalkylhydantoins must be unprotected in a complicated manner before an enzymatic conversion. The protective groups to be used thereby belong to the state of the art (Barton/Oll is "Comprehensive Organic Chemistry" vol. 5 p. 333, Pergamon Press, Oxford, 1979; Chem. Abstr. 110 (1989) 135715x; Chem. Abstr. 190 (1988) 6967m).

Examples are also known (Angew. Chem. 103 (1991) 704–706) for preparing certain amino acids such as D-citrulline from L-amino acids with the same C number, such as for example L-ornithine. For this, 2 equivalents cyanate are reacted with L-ornithine and the α,ω-bisureido compound is acidicly changed into citrulline hydantoin, which can be converted enzymatically to D-citrulline. However, the suggested synthesis pathway does not function with amino acids containing an amino function.

The present invention address the problem of creating a method of preparing α-amino acids or 5-substituted hydantoins with basic side chain in which the protection of the amino function in the side chain necessary during the formation of the hydantoin should require only the lowest expense possible in regard to the entire method.

This problem is solved by the measures of the invention.

The novel method is characterized in that on an α-amino acid with the general formula IV or its salt

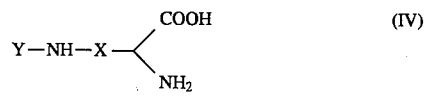

in which
- X and Y have the meaning indicated above and either a stereoisomeric mixture or the optical antipode to Formula II is used as α-amino acid or its salt. The X and Y adjacent to the amino function is protected prior to the formation of the hydantoin (I) with the amino protective group W which can be split off with acid when a compound of the general formula III or its salt is obtained.

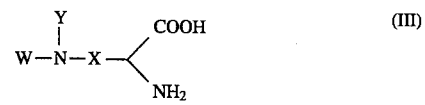

in which
- X and Y have the meaning indicated above and W signifies an amino protective group which can be split with acid, and that the compound of the general formula III resulting therefrom or its salt is caused to react with a cyanate and is cyclized by means of treatment with acid.

The formation of the hydantoin ring is possible in any desired manner in the present invention. The above-named variant starting with the amino acid, conversion with cyanate and cyclizing by means of the action of acid is preferred since the hydantoin that has been "deprotected" on the amino function is obtained directly thereby. The hydantoin formation is limited solely to the extent that an acid treatment during the conversion may not take place in the entire method until at a point in time at which an amino function can no longer participate in competing reactions. This is exemplifier in the case of the method starting with cyanohydrin and also in the case of the preferred method, the conversion with the cyanate. In the preferred method, during the acidic cyclizing the amino protective group is split off at the same time which, is especially advantageous since, as a result, the previously expensive deprotecting is totally eliminated. Although method steps with acid treatment can be contained in the present method, according to the invention no protective group which can be selectively split off is necessary for the protection of the X adjacent amino function.

For the preparation of the aminoalkyl-α-amino acid the received hydantoin can be converted further as initially described. The enzymatic splitting to the stereospecific amino acids or carbamoylized amino acids is preferred thereby since the chemical hydantoin splitting results in the racemate. The fact is also especially advantageous thereby that under certain (alkaline) conditions the hydantoin not converted by the enzyme is racemized and a total conversion to the amino acid is achieved as a result thereof. In particular, D-antipodes of natural amino acids such as, for example, D-lysine or D-ornithine as well as also the antipodes of non-natural amino acids such as thialysine, oxalysine, albiciine and others can be obtained with the present method. These amino acids are increasingly used in the area of pharmacology and as racemate splitting agents. They are not metabolized or metabolized only slightly by the body and are therefore suitable for increasing the stability of medicines. For example, polymers of D-lysine can be used as racemate splitting agents (Lahav et al., Reactive Polymers 6, 241–253 (1987).

As has already been explained, the hydantoin synthesis can take place in accordance with the present invention by reacting a compound of the general formula III

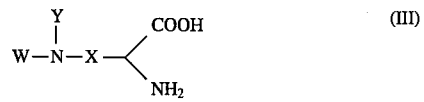

in which
W signifies an amino protective group such as for example trifluoroacetyl or t-butyloxycarbonyl which can be split with acid and, X and Y have the meaning indicated above, with cyanate to carbamoyl amino acid, which is subsequently cyclized in an acidic method step to hydantoin. The protective group W is split off at the same time thereby and the compound of general formula I obtained.

The protective group W is necessary since otherwise the amino function would likewise be carbamoylized during the reaction with cyanate. The method of the invention avoids an additional, expensive reaction step, catalyst expenses and further waste since the benzyloxycarbonyl protective customarily used for the hydantoin formation is removed by hydrogenation.

In the above general formulas Y—NH—X— preferably stands for $H_2$—$(C_1$–$C_6)$-alkyl-; in particular, D-lysine and D-ornithine can be prepared in an advantageous manner with the present invention.

The invention will now be explained in detail using a schema and in the following examples.

The scheme shows by way of example the preparation of D-lysine starting from L-lysine.

BRIEF DESCRIPTION OF THE DRAWINGS

The FIG. shows the preparation of the D-lysine from L-lysine.

EXAMPLE 1

Synthesis of 5-(4'-aminobutyl)-L-hydantoin 24.2 g (0.1 mole) $N^\varepsilon$-trifluoroacetyl-L-lysine are suspended in 100 ml water. 7.15 g (0.11 mole) NaOCN are added and heated for 4 h at 70°–75° C. The mixture is then cooled down to 40° C. and adjusted with conc. HCl to pH 4–5. 16.5 ml conc. HCl are now added and the mixture is boiled 4 h under reflux. The solution is filtered after having cooled down via an acidic ion exchanger (Merck IR 120, $H^+$ form) and subsequently eluated with aqueous ammonia. This eluate is concentrated by evaporation to a large extent and compounded with ethanol (50 ml). The precipitating solid is filtered and dried in a vacuum.

Yield 13.95 g (82% of theory).

EXAMPLE 2

Reaction of 5-(4'-aminobutyl)-L-hydantoin with Agrobacterium radiobacter 4 g 5-(4'-aminobutyl)-L-hydantoin are dissolved in a pressurized container in 66 ml water. A pH of 8.2–8.3 is adjusted by adding HCl. After the addition of 6.5 g biomass (Agrobacterium radiobacter; Recordati/De. Bi, Milan, Italy) the mixture is degassed with $N_2$ and a superpressure of 2–4 bar adjusted. The mixture is allowed to react 48 h at 40° C., the biomass centrifuged off and the centrifugate clarified at pH 6 with activated carbon. The mixture is then desalinated on an acidic ion exchanger (Merck IR 120, $H^+$ form). The ammoniacal eluate is concentrated in a vacuum to a residual volume of 10 ml, adjusted with HCl to pH 2 and compounded with 40 ml ethanol.

Yield: 3.7 g D-lysine hydrochloride (87% of theory).

EXAMPLE 3

(Comparable example with the protected hydantoin)

Conversion of 5-(4'-(N-carbobenzoxy-amino)-butyl)-L-hydantoin with Agrobacterium radiobacter 4 g 5-(4'-(N-carbobenzoxy-amino)-butyl)-L-hydantoin were reacted in analogy with example 2.

Exclusively educt was isolated and no conversion reaction took place.

What is claimed is:
1. A method of preparing 5-(aminoalkyl)-hydantoin of the formula I or the aminoalkyl-α-amino acid of the formula II or their salts obtainable from them

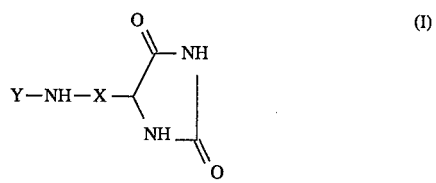

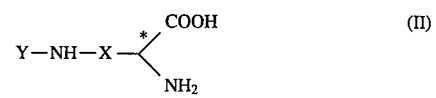

in which
X stands for a $C_1$–$C_6$ alkylene group a $C_1$–$C_6$ alkylene group interrupted by oxygen or sulfur with preservation of adjacent amino function, and Y stands for hydrogen, $(C_1$–$C_4)$ alkyl or benzyl and * signifies an optically pure compound on the α-C atom, in which method an α-amino acid with the formula IV or its salt

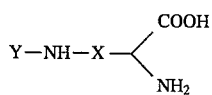

in which

X and Y have the meaning indicated above and either a stereoisomeric mixture or the optical antipode to II is used as α-amino acid or its salt, wherein X and Y are adjacent to the amino function is protected with the amino protective group W splittable off with acid when a compound of the formula III or its salt is obtained

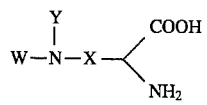

in which

X and Y have the meaning indicated above and W signifies an amino protective group which is acid labile, characterized in that the amino protective group W is introduced before the formation of the hydantoin (I) and the compound of the formula III resulting therefrom or its salt reacts with a alkali cyanate and cyclized by means of treatment with acid.

2. The method according to claim 1, characterized in that the splitting off of the amino protective group W takes place with the acid treament.

3. The method according to claim 2, characterized in that trifluoroacetyl or t-butyloxycarbonyl is used as amino protective group W which can be split with acid.

4. A method according to claim 1, characterized in that the hydantoin is split enzymatically into the amino acid or N-α-carbamoyl amino acid.

5. A method according to claim 1, characterized in that the in that the Y—NH—X— stands for $H_2N—(C_1–C_6)$-alkyl—.

* * * * *